(12) United States Patent
Kayerod

(10) Patent No.: US 8,458,812 B2
(45) Date of Patent: Jun. 11, 2013

(54) PROTECTIVE FACE MASK

(75) Inventor: Helle Kayerod, Naerum (DK)

(73) Assignee: Kreaps APS, Naerum (DK)

( * ) Notice: Subject to any disclaimer, the term of this patent is extended or adjusted under 35 U.S.C. 154(b) by 128 days.

(21) Appl. No.: 12/857,052

(22) Filed: Aug. 16, 2010

(65) Prior Publication Data

US 2010/0306893 A1 Dec. 9, 2010

Related U.S. Application Data

(63) Continuation of application No. 11/896,127, filed on Aug. 29, 2007, now Pat. No. 7,774,858.

(60) Provisional application No. 60/840,691, filed on Aug. 29, 2006.

(51) Int. Cl.
*A41D 19/00* (2006.01)

(52) U.S. Cl.
USPC ............................................. 2/9; 2/15; 2/174

(58) Field of Classification Search
USPC .................................................. 2/9, 15, 174
See application file for complete search history.

(56) References Cited

U.S. PATENT DOCUMENTS

| | | | |
|---|---|---|---|
| 1,640,676 A | 8/1927 | Eppers, Shaeffer Julia | |
| 2,033,691 A * | 3/1936 | Douglass | 2/174 |
| 3,310,812 A * | 3/1967 | Gaisser | 2/9 |
| 3,339,546 A | 9/1967 | Chen | |
| 4,367,732 A | 1/1983 | Poulsen et al. | |
| 4,635,625 A | 1/1987 | Teeple | |
| 4,856,535 A * | 8/1989 | Forbes | 128/857 |
| 4,890,608 A * | 1/1990 | Steer | 602/57 |
| 5,685,022 A * | 11/1997 | Essman et al. | 2/434 |
| 5,865,196 A * | 2/1999 | Foote | 132/319 |
| 7,774,858 B2 * | 8/2010 | Kayerod | 2/9 |

FOREIGN PATENT DOCUMENTS

| | | |
|---|---|---|
| AT | 8 226 B | 7/1902 |
| CH | 127 130 A | 8/1928 |
| EP | 1 214 896 A1 | 12/2000 |
| WO | WO 99/30583 A1 | 6/1999 |
| WO | WO 2004/190912 A2 | 5/2004 |
| WO | WO 2005/033198 A1 | 4/2005 |
| WO | WO 2005/110147 A1 | 11/2005 |

* cited by examiner

*Primary Examiner* — Katherine Moran

(74) *Attorney, Agent, or Firm* — Birch, Stewart, Kolasch & Birch, LLP

(57) ABSTRACT

A protective face mask includes an eye-protecting shield made essentially from a plastics material. The eye-protecting shield is dimensioned to cover at least the eye portions of a human wearer. The eye-protecting shield has a perimeter defining a first surface facing the wearer's face, and a second surface facing away from the wearer's face. An adhesive forms an adhesive strip attached to the first surface of the eye-protecting shield for providing a substantially watertight and releasable sealing engagement between at least a portion of the perimeter forming an upper edge of the face mask and at least a portion of the skin of the wearer's face.

17 Claims, 10 Drawing Sheets

PROTECTIVE FACE MASK

CROSS REFERENCE TO RELATED APPLICATIONS

This application is a Continuation of application Ser. No. 11/896,127, now U.S. Pat. No. 7,774,858, filed on Aug. 29, 2007, which claims priority to U.S. Provisional Application No. 60/840,691, filed on Aug. 29, 2006. The entire contents of all of the above applications is hereby incorporated by reference.

BACKGROUND OF THE INVENTION

The present invention relates to a face mask comprising a protective eye shield dimensioned to cover at least the eye portions of a human wearer. The face mask is particularly useful for shielding against water or shampoo during showering and hair washing. The face mask is also applicable in hairdressing for protecting the wearer's eyes from hair tonic, rinse, hair spray, hair colour and clippings, or in the area of leisure, e.g. for protecting bikers', runners' or hikers' eyes from rain, wind, sun and bugs.

1. Field of the Invention

Eye goggles and face masks are habitually used to keep the wearer's eyes protected from external environments. For example, swimming goggles are used to protect the wearer's eyes from water.

2. Description of the Related Art

Traditional eye goggles and face masks normally comprise a spongy or rubber-like material for providing a seal between a perimeter of the goggles or face masks and a portion of the face surrounding the wearer's eyes. Such goggles and face masks are typically made of a rigid plastic material. The eye goggles or face masks may be held in place, firmly engaging the wearer's face, by head straps or elastic bands. Goggles and face masks are traditionally sealed around the entire eye contour of the wearer. The sealing can cause pressure on the skin in the contact zone between the seal and the skin, thereby causing restrictions on eye contour movements. The sealing may further cause pressure marks on the skin.

An alternative type of eyewear is known from WO 2004/010912, disclosing a lens adapted to cover at least one of a user's eyes, and a sealing frame adjacent the perimeter of the lens for generally providing protection to the eyes of a user during use by isolating the user's eyes from the outside environment. In one embodiment, the frame is compliant and resiliently deformable and adapted to form a seal between the frame and at least a portion of the user's face along the perimeter of the lens. The frame has an adhesive side disposed partially beyond the perimeter of the lens and adapted to adhere releasably to a portion of the user's face.

U.S. Pat. No. 4,856,535 discloses a shield for providing a water proof seal across the forehead and along the sides of the face shield to allow a patient having recently had facial cosmetic or reconstructive surgery to shower and shampoo their hair while keeping the bandages and incisions in a clean dry condition. The edge of the shield having the adhesive is, in the preferred form, pressed against the patient's forehead adjacent the hairline and down along the temples and the side of the face. The shield is of a flexible material allowing the bending and forming along the contour of the face while being rigid enough to retain its shape and form a shield spaced from the patient's face, and produces a tent-like structure leading away from the forehead downwardly over the nose and extending beyond the chin of the patient. As the shield disclosed in U.S. Pat. No. 4,856,535 extends beyond the chin of the patient humidity from exhaled air will condense at the inner surface thereof and form dew being highly undesirable, especially if used for protecting children's eyes, nose and mouth during bathing. Furthermore, children may feel isolated behind a full face mask covered with dew.

A device for protecting certain facial areas is known from WO 2005/110147. The device comprises a transparent shield and an adhesive area for fastening the device on the face of an individual, said adhesive area being applied to the shield in a border area thereof. The adhesive area is configured by a plurality of adhesive points thereby providing an protection against fine cut hair during hair cut at hairdressers.

SUMMARY OF THE INVENTION

It is an object of preferred embodiments of the present invention to provide a comfortable, flexible face mask that provides a shield for the wearer's eyes without the need for straps, elastic bands or side bars for keeping the face mask in place, said face mask being comfortable and easy to use.

It is a further object of preferred embodiments of the present invention to provide a face mask, which avoids pressure on the skin in the contact zone between seal and skin, and which allows free eye movement.

Still further it is an object of the invention to provide a face mask which allows for free airflow to the eye region and nose and mouth allowing free breathing through the nose and the mouth, and which minimizes the inconvenience of dewing on the surfaces of the mask and leaves the jaw area free enabling unhindered jaw movement, e.g. when speaking.

A yet further object of the invention is to provide a face mask which in use directs water to one or both sides of the face for avoiding water flowing from the mask in front of the nose and the mouth.

DETAILED DESCRIPTION OF THE PRESENT INVENTION

In a first aspect the present inventions provides a protective face mask comprising:
  an eye-protecting shield made essentially from a plastics material, the eye-protecting shield being dimensioned to cover at least the eye portions of a human wearer, the eye-protecting shield having a perimeter defining a first surface facing the wearer's face, and a second surface facing away from the wearer's face;
  an adhesive forming an adhesive strip attached to the first surface of the eye-protecting shield for providing a substantially watertight and releasable sealing engagement between at least a portion of the perimeter forming an upper edge of the face mask and at least a portion of the skin of the wearer's face, wherein
  the upper part of the perimeter of the mask is provided with a continuous layer of adhesive along the perimeter, and the lower part of the perimeter of the mask is free of adhesive,
  the lower part of the perimeter forms a bottom edge of the mask being provided with at least one part forming a projection offset from the centre line of the mask, and wherein
  the mask extends along the contour of the wearer's face from the forehead to cheekbones and the lower perimeter thereof extends above the mouth.

The face mask of the invention fulfils the above-mentioned objects and is in the form of a simple and cheap product which is easy to manufacture and use and more comfortable than the masks of the state of the art, especially the mask disclosed in U.S. Pat. No. 4,856,535. It has been found that the problems with condensation are minimized using the mask of the invention. It has been found that the lower edge of the face mask should extend to a level above the upper lip in order to interfere with exhaled air. Typically it will be suitable that the lower edge of the mask extends no more than about 2 centimetres below the tip of the nose in order to minimize formation of dew at the surface facing the wearer.

In a preferred embodiment of the face mask the lower perimeter thereof extends above the tip of the nose. This embodiment is preferred for use for e.g. children or for adults closing the mouth when bathing.

The at least one projection may be sharp-pointed or preferably have a convex shape.

In a preferred embodiment of the invention the lower part of the perimeter of the mask is provided with a convex-concave-convex bottom edge having two convex parts forming projections offset from the centre line of the mask providing a safe draining of water avoiding water flowing from the mask in front of the nose and the mouth.

In another embodiment of the invention the upper part of the perimeter of the mask generally has a convex shape giving an easier and better adaptation to the shape of the forehead and also assists in directing water around the nose and the mouth.

In preferred embodiments, the eye-protecting shield is made from one single piece of material, with the adhesive being attached to the first surface of the single-piece eye-protecting shield. It will hence be appreciated that the face mask may be frameless, and that embodiments of the invention hence may be more flexible, light and compliant than the eyewear disclosed in WO 2004/010912 and furthermore avoids the problems formation of dew for the face mask disclosed in U.S. Pat. No. 4,856,535.

In another preferred embodiment, the eye-protecting shield is made from two pieces of material, the eye-protecting shields each being dimensioned to cover at least one eye portion of a human wearer, with the adhesive being attached to the first surface of the eye-protecting shields.

It should be understood that the single piece of material may comprise adhesively bonded layers or layers which are joined by any other techniques known per se. It should further be understood that the adhesive may be provided as a layer to the first surface of the eye-protecting shield (or "lens"), the thickness of the layer suitably being approximately in the range of that of the plastics material of the eye-protecting shield, for example a thickness of 0.01-2.5 mm. Alternatively, the eye-protecting shield may have a thickness of approximately 0.01-2.5 mm, with the adhesive layer having a thickness of approximately 0.01-1.0 mm. In other embodiments, the eye-protecting shield may have a thickness of approximately 0.01-1.0 mm, with the adhesive layer having a thickness of approximately 0.01-2.5 mm.

Embodiments including two components only, i.e. the single-piece eye-protecting shield and the adhesive attached thereto provide a simplified construction. Generally, the simple structure of the face mask of the present invention allows it to be manufactured at low cost, while being light, comfortable and easy to use, e.g. for protecting the wearer's eyes during treatment or washing of the wearer's hair.

The adhesive is preferably provided as a band or strip extending along or adjacent the perimeter of the eye-protecting shield. In one embodiment, the band or strip may lie flush with the perimeter of the shield without extending beyond the perimeter, whereas in other embodiments, it may be retracted a distance of, e.g. approximately 0.1-5 mm from the shield perimeter.

The face mask may be disposable, i.e. for single use only, or it may be re-usable. In order to ensure re-usability or re-fitting of the face mask, an adhesive providing a resealable sealing engagement with the skin of the wearer's face may be used.

According to a second aspect, the invention relates to the use of an adhesive selected from a group consisting of hydrocolloid, hydrogel and any combination thereof for attaching a face mask to a face of a human wearer.

Other adhesives with similar characteristics may also be used.

In a preferred embodiment the adhesive is capable of adhering to wet and/or substantially dry skin enabling the application of the face mask after commencing bathing.

It is suitable for the purpose of the present invention to use an adhesive selected form the group consisting of hydrocolloid adhesives, hydrogel adhesives and any combination thereof.

In an embodiment of the invention is used an adhesive which provides a resealable sealing engagement with the skin of the wearer's face enabling a reuse of the face mask e.g. for home use when bathing children.

The sealing structure or adhesive may e.g. comprise one or more skin-friendly adhesives such as a hydrocolloid adhesive, commercially available from Coloplast A/S, 3050 Humlebæk, Denmark, under the trade name Curagard™. The adhesive may comprise hydrocolloid adhesives as described in U.S. Pat. No. 4,367,732 "Skin barrier" (Coloplast A/S) and/or U.S. Pat. No. 3,339,546 "Bandage for adhering to moist surfaces" (Squibb) which are hereby incorporated by reference. In another embodiment, the adhesive may be applied to wet skin using a skin-friendly hydrogel adhesive such as First Water hydrogel adhesive, commercially available from First Water Ltd., Wiltshire, UK, under the trade name Gel 20 hydrogel. Another hydrogel adhesive which may be used is described in WO 2005/033198 "A composition useful as an adhesive and use of such a composition" (Coloplast A/S) which is hereby incorporated by reference.

Such adhesives have been developed with the primary aim of attaching stoma systems to the abdominal skin portions of stoma patients and for protecting skin areas and parts of the body against pressure impact and friction. However, the present inventor has found that they are also suitable for application to face masks as disclosed herein. Generally, the adhesive may be provided as a coating on a surface of the shield or as a tape attached thereto.

An alternative suitable adhesive is available from 3M Corporation as product No. 1526.

Embodiments of the invention may include several types of adhesives provided e.g. in adjacent bands on a surface of the shield, thereby combining the benefits and advantages of several adhesives in a single product.

The adhesive preferably comprises a flexible adhesive structure, including a comparatively thin layer of adhesive, cf. the above considerations regarding layer thickness compared to shield thickness. In another preferred embodiment the thickness of the adhesive layer is approximately in the range of the plastics material of the eye-protecting shield.

In order to secure eye contour movement and free air flow across wearer's eye region, the adhesive may be attached to an upper part of the perimeter of the face mask only, leaving a lower part of the perimeter free of adhesive. Thereby, the wearer's eyes may be efficiently protected thanks to the watertight seal between the wearer's forehead and the protecting shield, while a complete isolation from the outside environment is avoided.

In a further embodiment the face mask according to the invention is provided with an expandable layer between the adhesive strip and the shield, said expandable layer being provided with one or more pockets or cells having at least one opening adjacent to the upper edge of the mask. In use, water will fill the pockets and lift the mask from the fore head and thus assist in avoiding that the face mask touches the eyelashes giving rise to nuisance, especially for children.

It is preferred that the expandable layer comprises a series of individual pockets giving a relatively flat product and providing a homogeneous lift across the forehead.

In one embodiment of the invention is used an expandable layer comprises a series of interconnected pockets assisting in providing a homogeneous lifting of the face mask. In a further embodiment of the invention is used an expandable layer comprising sections of interconnected pockets.

It is also considered an embodiment of the invention to provide the inner side of the pockets or cells with a hydrophilic coating for facilitating the entering of water.

In a still further embodiment of the invention the central part of the bottom edge of the mask is provided with a gutter system for guiding water from the centre of the face. Such a system will direct water away from the nose and mouth region along the lower edge of the mask, preferably to one or more projections facilitating the draining off from the mask.

It is desirable that the protective shield and thus the face mask is flexible and light. The eye-protecting shield should preferably be sufficiently light and flexible to allow it to conform comfortably to the shape and contour of the wearer's face in the region of the wearer's eyes and nose. The face mask, or at least a major portion of the eye-protecting shield, may be transparent, allowing the wearer to view through the shield.

There may be provided a printed or coloured portion on at least one of the first and second surfaces, e.g. with the purpose of identifying the wearer. If, for example, the face mask is used during sport competitions, the printed or coloured portion may allow identification of the wearer or the team to which he/she belongs. Alternatively, the printed portion may include instructions for use, e.g. instructions illustrating removal of a release liner optionally protecting the adhesive. Alternatively, the printed or coloured portion may provide commercial advertisements, or they may have purely decorative purposes. A release liner may be any release liner known per se, e.g. for protecting ostomy or wound care appliances.

In a preferred embodiment of the invention the plastics material of the eye-protecting shield is provided with a coating with one or more coatings selected from the group consisting of:
  coatings protecting against ultra-violet penetration;
  coatings providing water-shedding or hydrophobic properties; and
  coatings providing anti-dew properties.

It is also considered a part of the invention to provide the face mask of the invention with further coatings which e.g. protects viewers of eclipses of the sun from damaging the eyes or to provide the mask with different colours a red part in front of one eye and a green part in front of the other eye to enable the provision of printed three-dimensional pictures.

The face mask according to the invention may be provided with a projection removal grip located on the same level as the end of the adhesive strip for facilitating the removal of the mask. Such a grip is preferably located at the end of the adhesive strip for peeling the mask from the face along the adhesive strip and essentially perpendicularly thereto minimizing the peel force and the straining of parts of the face. In one embodiment the grip is located at the left side of the mask for convenience for right-handed assistants such as parents bathing children or alternatively the grip is located at the right side of the mask for convenience for left-handed assistants (parents).

It is preferred to provide the mask with a release-liner provided with a projecting removal grip located on the same level as the face mask's removal grip and having an edge protruding from the adhesive layer for facilitating the removal thereof from the adhesive surface before application.

BRIEF DESCRIPTION OF THE DRAWINGS

The invention is disclosed more in detail with reference to the drawings in which.

DESCRIPTION OF THE PREFERRED EMBODIMENTS

The invention is now explained more in detail with reference to the drawings showing preferred embodiments of the invention but which are not to be construed as limiting the scope of the invention as set forth in the appended claims.

Figure 1:
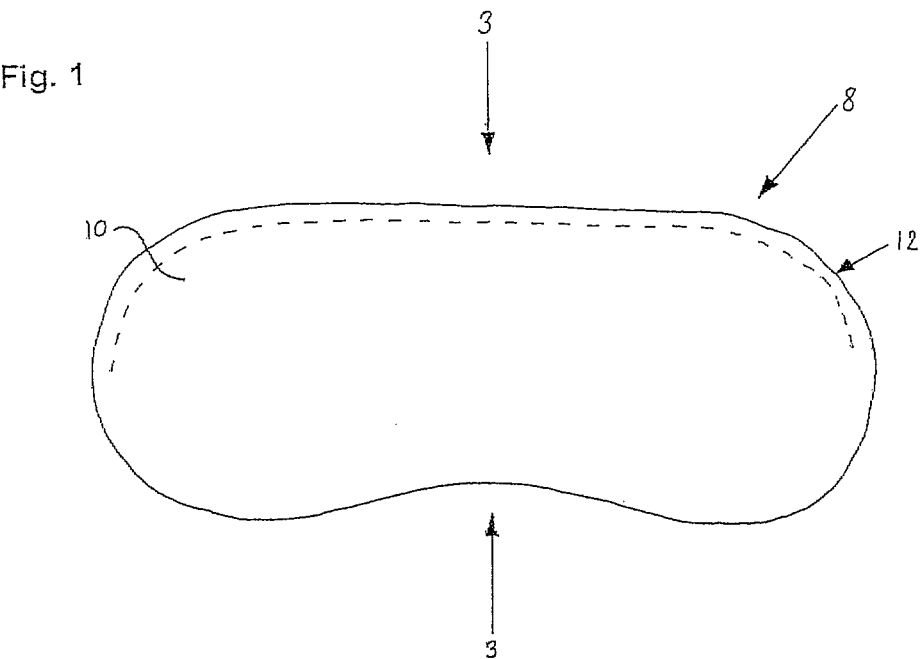
FIG. 1 is a top plan view of an embodiment of the present invention.
Figure 2:
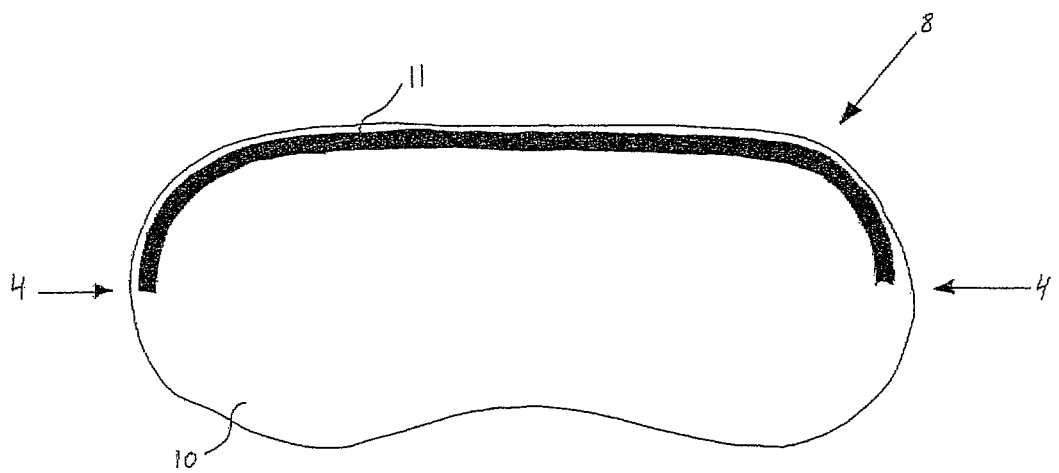
FIG. 2 is a bottom plan view of an embodiment of the present invention.

FIGS. 1 and 2 show a face mask 8 in accordance with the present invention. The face mask 8 generally provides protection against liquids such as soap and water or rain, wind, bugs, sun or light without sealing off the entire eye contour and without the use of elastic bands, head straps and side bars and furthermore without sealing off the side of the face and the jaw area. The face mask comprises a plastic shield 10, to a surface of which there is provided an adhesive strip 11. At least a portion and preferably the entire plastic shield 10 is transparent. The shield material is flexible and light, so that it easily conforms to the wearer's face. The adhesive strip 11 comprises one or more adhesives that can adhere to wet and/or dry skin. The adhesive strip forms a continuous watertight seal between the shield 10 and a portion of the user's face.

Suitable materials for the eye-protective shield of the invention are transparent flexible materials like e.g. a polyurethane film (PU). The shield is preferable a thin, transparent, flexible plastic material which may be essentially planar or shaped in three dimensions. It is preferably shaped and sized such that the perimeter of the shield extends along with and in contact with the contour of the wearer's face from the forehead to cheekbones and nose tip. Other suitable plastic materials are acryl ester materials such as PMMA, polystyrene materials, polycarbonates or polyolefins such as polyethylene of polypropylene or polyvinyl chloride.

For example, the shield may be made from a single sheet of polyurethane film, optionally surface-treated and/or coated and provided with the adhesive.

A suitable material for the adhesive strip 11 is a flexible, compliant, skin-friendly adhesive material having a "fast tack" that is easy to apply to the users face and easy to remove from the users face after use. In one embodiment of the invention, the adhesive comprises one or more skin-friendly adhesives such as a hydrocolloid adhesive, commercially available from Coloplast A/S, 3050 Humlebæk, Denmark under the tradename Curagard™. In another embodiment, the adhesive strip 11 comprises hydrocolloid adhesives as described in U.S. Pat. No. 4,367,732 "Skin barrier" (Coloplast A/S) and/or U.S. Pat. No. 3,339,546 "Bandage for adhering to moist surfaces" (Squibb). In a third embodiment, the adhesive strip 11 can be applied to wet skin using a skin-friendly hydrogel adhesive such as First Water hydrogel adhesive, commercially available from First Water Ltd., Wiltshire, UK, under the trade name Gel 20 hydrogel. In yet another embodiment, the adhesive strip 11 is a hydrogel adhesive as described in WO 2005/033198 "A composition useful as an adhesive and use of such a composition" (Coloplast A/S). Embodiments of the invention may include several types of adhesives provided e.g. in adjacent bands on a surface of the shield, thereby combining the benefits and advantages of several adhesives in a single product. Suitable reusable adhesives are e.g. silicone adhesives known for use for applying external breast prostheses.

Figure 3:
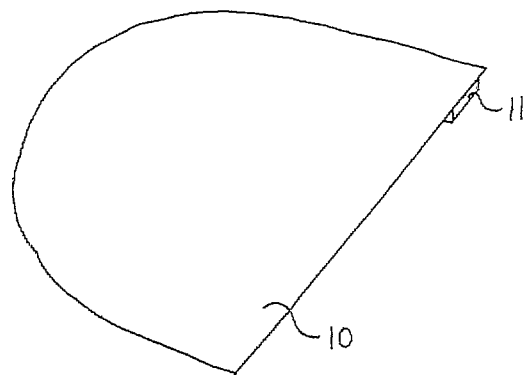
FIG. 3 is a cross-sectional view along line 3-3 of FIG. 1 in the area of the adhesive strip.
Figure 4:
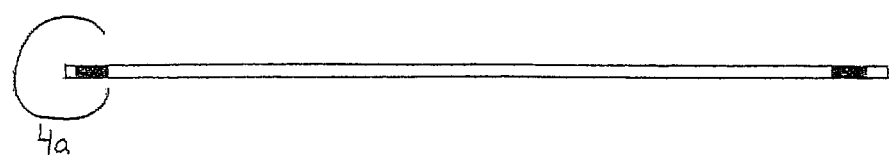
FIG. 4 is a cross-sectional view of an embodiment of the present invention along line 4-4 of FIG. 2.
Figure 4A:
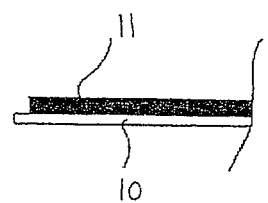
FIG. 4a is a partial, magnified cross section of a side of the embodiment of FIG. 4.

In FIGS. 4 and 4a, the adhesive strip 11 is shown disposed adjacent to the edge of the shield 10. As shown in FIG. 4a, shield 10 extends beyond the adhesive strip 11, but the adhesive strip may also continue all the way to the edge, i.e. lie flush with the perimeter of the perimeter of the shield. The adhesive strip 11 is shown with exaggerated thickness in FIG. 3.

Figure 5:
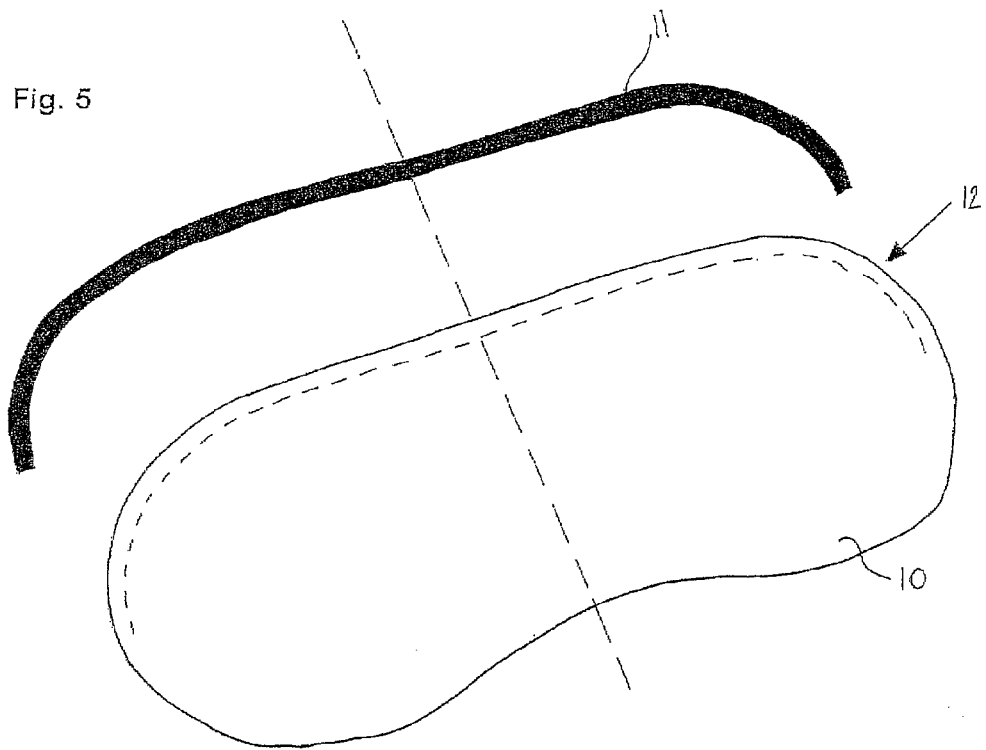
FIG. 5 is an exploded view of an embodiment of the present invention.

FIG. 5 shows the construction of an embodiment of the face mask 8 which comprises two components, a shield 10 and an adhesive strip 11, where the adhesive strip extends along the perimeter 12 of the shield 10 as indicated by the dotted line. The adhesive strip comprises one or more adhesives as discussed above.

Figure 6:
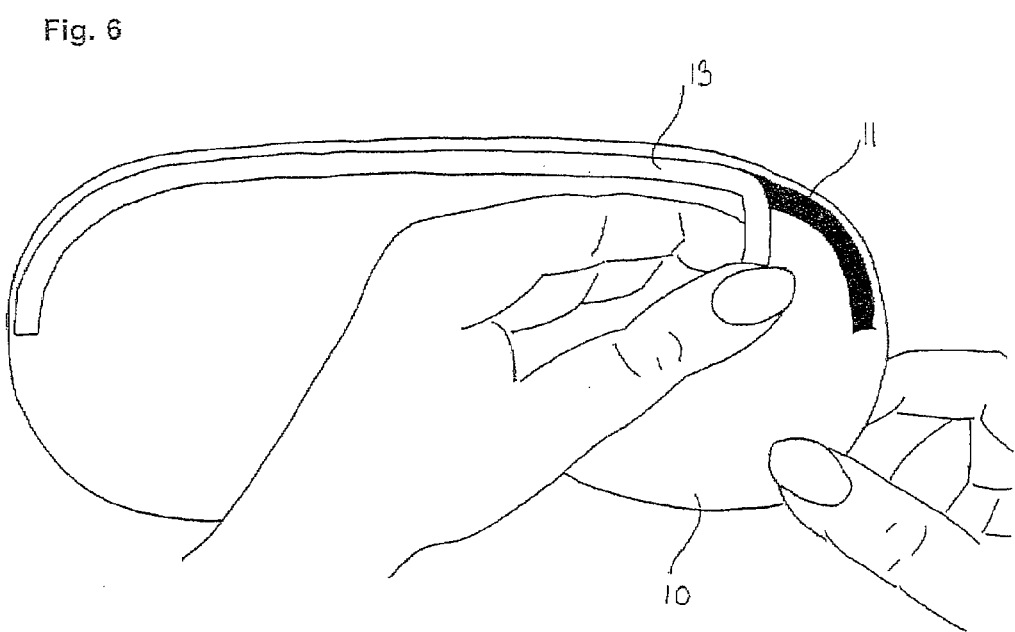
FIG. 6 is a pictorial view of removal of release liner.

As shown in FIG. 6, the adhesive strip 11 may be protected by a removable release liner 13 to be removed before applying.

Figure 6A:
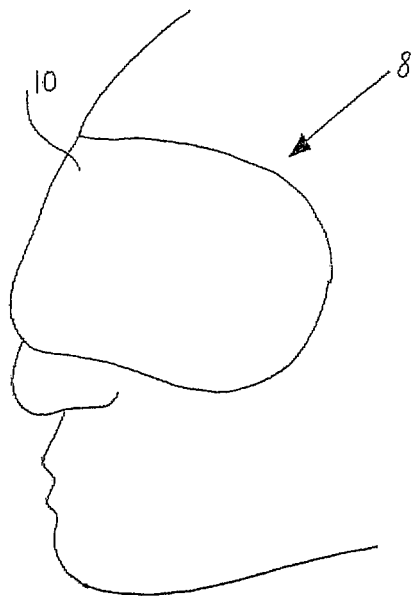
FIG. 6a is a perspective view of an embodiment of the present invention.

FIG. 6a shows a perspective view indicating the size and placing of an embodiment of a face mask of the invention when used in showering.

Figure 7:
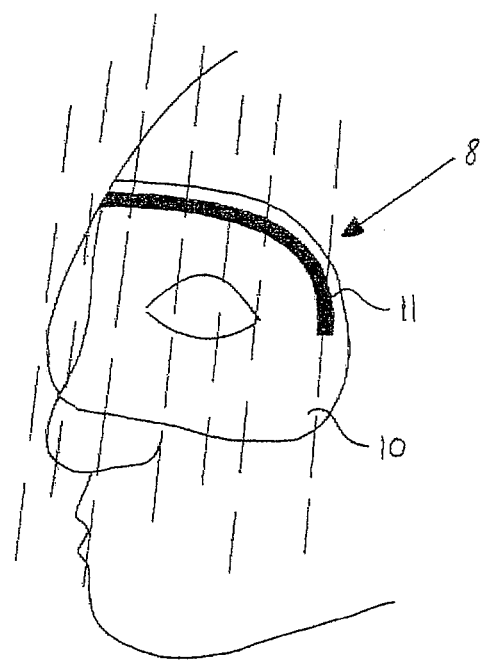
FIG. 7 is a pictorial cross section of a face mask according to the present invention as worn by a wearer.

In FIG. 7, the face mask 8 is illustrated in use. A transparent plastic shield 10 covers the wearer's eyes and is retained in place by the adhesive strip 11. FIG. 7 illustrates how the eyewear 10 protects the wearer's eyes without sealing off the entire eye contour, providing free eye contour movements and air supply to the eyes. FIG. 7 also illustrates the free access to the user's hair during use of the face mask 8 and also illustrates that the jaw area is free and enables unhindered movement of the jaw, e.g. when speaking.

Figure 8:
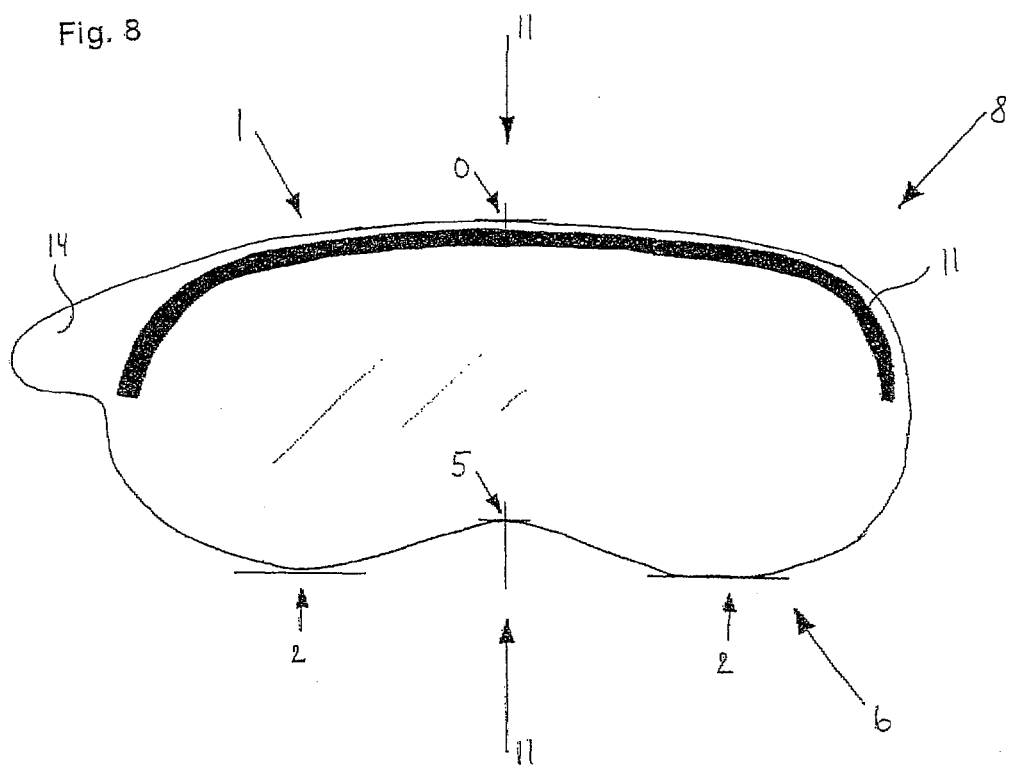
FIG. 8 is a bottom plan view of another embodiment of the present invention.
Figure 9:
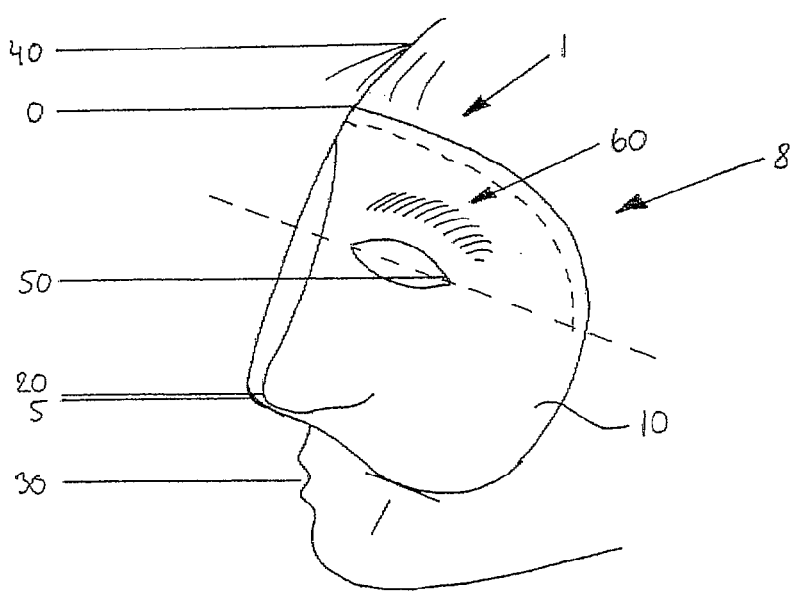
FIG. 9 is a pictorial cross section of another face mask according to the present invention as worn by a wearer.

FIGS. 8 and 9 show another embodiment of a face mask 8 in accordance with the present invention. The face mask generally provides protection against liquids such as soap and water, or rain, bugs, sun, light without sealing off the entire eye contour and without sealing off the jaw area and without the use of elastic bands, head straps and side bars. The face mask is suitably made from the same materials as stated above.

The face mask 8 has a slightly convex upper edge 1, said upper edge following the shape of the forehead, having a top point 0 and having a convex-concave-convex (wave shaped) bottom edge 6. The distance between the lower concave point 5 (upper wave point 5) and the convex point 2 (lower wave point 2) should suitably be from 0.5 to 2 cm, e.g. about 1 cm. The water will then be directed away from the nostrils and towards the convex points 2 of the mask, essentially preventing water from falling or dripping in front of the nose and mouth.

The lower concave point 5 should as a minimum start at the tip of the nose 20 and maximum start at the level of the mouth 30 (typically offset about 3 cm from the nose) to prevent dewing and moist to develop inside the shield from humidity of exhaled air. The distance between the top point 0 and the lower concave point 5 is suitably so that it covers the face from the forehead to minimum the nose tip 20, and preferable no longer than the level of the mouth 30 (normally from about 8.5 cm to about 11.5 cm) depending on the size of the head of the intended user.

The side edges 7 of the face mask 8 follow the shape of the face from the temple down to the cheekbones continuing into the convex-concave-convex (wave shaped) bottom edge 6. The distance between the side edges 7 is minimum so, that the mask can be applied without inducing pressure on the nose bone from the plastic shield 10, and at the same time allows the plastic shield 10 to lift up and free of the nose bone to improve air flow within the mask and secure a clear visual (suitably from about 16 to about 22 cm).

FIG. 9 illustrates the face mask 8 in use. The face mask 8 is preferably placed slightly above the eyebrows 60, avoiding getting too close to the hair-line 40, so hair is not caught between the face mask 8 and the forehead.

The adhesive band indicated by 11 is designed to follow the upper slightly convex edge 1 until the level of the corner of the eyes 50, providing a watertight seal between the forehead and the plastic shield 10 without aggravating eye contour movement and jaw movements (especially children are active, moving and talking a lot, so it is important that the adhesive does not extend below the cheekbone in order to avoid skin irritation from mechanical movement of the jaw), and securing an easy and safe application due to the short length of the adhesive band 11.

Figure 10:
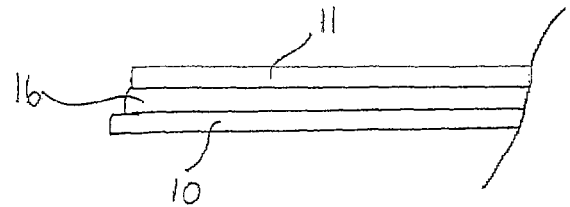
FIG. 10 is a partial, magnified cross section of a side of the embodiment of the present invention with water pockets.

In FIG. 10 is shown a part of an embodiment of the invention having an adhesive strip 11 disposed adjacent an expandable layer 16 comprising the water pockets, and the layer 16 is shown disposed adjacent the shield 10. In the embodiment shown the shield 10 extends beyond the layer 16 comprising water pockets, but the layer 16 comprising water pockets may be placed adjacent to the edge, i.e. lie flush with the perimeter of the perimeter of the shield 10 or even extend beyond the shield 10. The layer 16 comprising water pockets extends beyond the adhesive strip 11, but alternatively the adhesive strip may continue all the way to the edge of the water pockets 16, i.e. lie flush with the perimeter of the water pockets.

Figure 10A:
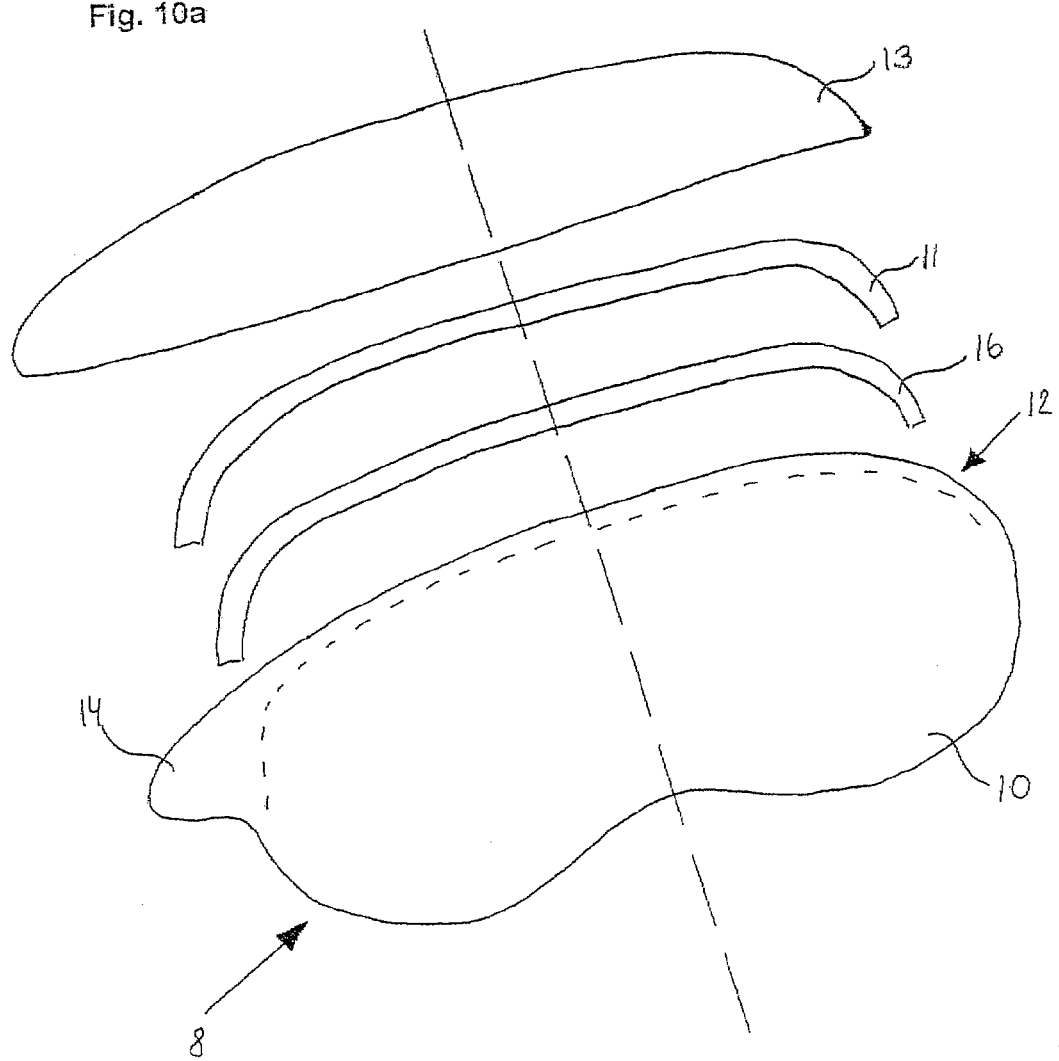
FIG. 10a is an exploded view of an embodiment of the present invention with water pockets.

FIG. 10a shows an exploded view of the construction of an embodiment of the face mask 8 which comprises four components, a shield 10 with an expandable layer 16 comprising water pockets that extends along the perimeter 12 of the shield 10, an adhesive strip 11 extending along the perimeter 12 on top of the layer 16 comprising water pockets, and a release-liner 15 that extends along the upper slightly convex edge 1 from the point 110 just below the removal grip 14 on the face mask 8 till the point 110 on the opposite side.

The adhesive strip may comprise one or more adhesives as discussed under FIGS. 4 and 4a.

In this embodiment it is preferred that the removal grip 14 is located at the level of the ends 110 of the adhesive strip.

Figure 11:
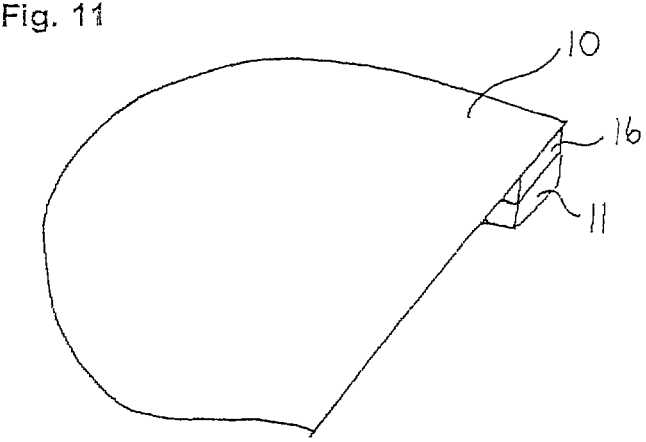
FIG. 11 is a cross-sectional view along the line 11-11 of FIG. 8 in the area of the adhesive strip and the layer with water pockets.

FIG. 11 shows a cross-sectional detail of the adhesive strip 11 and the water pockets 16 in an empty position, both shown with an exaggerated thickness, attached to the shield 10.

Figure 12A:
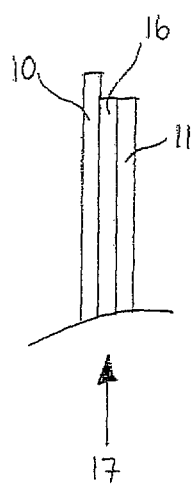
FIG. 12a is a partial, magnified cross section of a side of the embodiment of the present invention with empty water pockets.
Figure 12B:
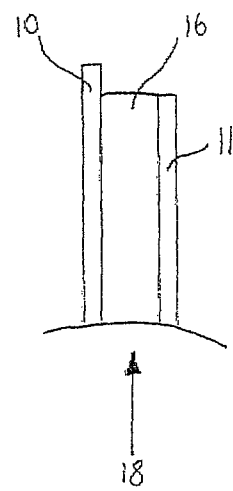
FIG. 12b is a partial, magnified cross section of a side of the embodiment of the present invention with full water pockets.

FIGS. 12a and 12b shows a cross-sectional detail of the adhesive strip 11 and the layer 16 comprising water pockets, attached to the shield 10. In FIG. 12a the layer 16 comprising water pockets the pockets are empty and preferable flat, so that the face mask 8 does not take up space i.e. the face mask 8 can be easily packed and transported. FIG. 12b shows the expanded layer 16 with water pockets, when filled with water. After the user has placed the face mask 8 on the forehead and enters the shower, the water pockets will be filled with water from the shower and expand the pockets from the flat position 17 in FIG. 12a to the expanded position 18 in FIG. 12b, thereby lifting the face mask 8 a distance 19 from the forehead. The lifting 19 will prevent that the shield 10 touches the eye-lashes, so free eye movement is secured and maximum comfort obtained.

Figure 13:
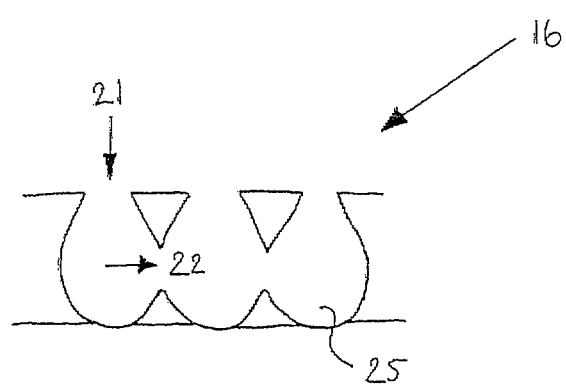
FIG. 13 is a cross sectional view of the water pockets.

In FIG. 13 a filling system of the water pockets is illustrated. The layer 16 comprising the water pocket system is preferable built on the concept of liquids free flow like it is known per se from e.g. ice-cube bags. The water enters through openings 21 and to secure a fast filling of all single pockets 25, the water will distribute in the layer comprising the pocket system through the openings 21 and transverse openings 22. The water pocket system may consist of one or multiple pockets 25, with one or more inlet openings 21, and with one or more transverse openings 22 connecting the pockets 25.

Figure 14A:
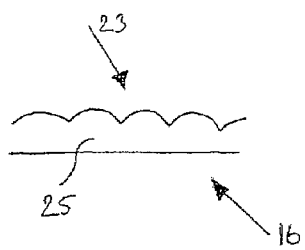
FIG. 14a is a cross sectional view of the top of multiple water pockets.
Figure 14B:
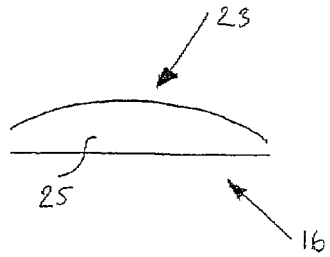
FIG. 14b is a cross sectional view of the top of one single water pocket.

FIGS. 14a and 14b show the surface 23 of the layer 16 comprising water pockets. In FIG. 14a the layer 16 consists of multiple water pockets 25. The layer 16 comprising the water pocket system preferable consists of several pockets 25, providing a multiple chamber-system. By using multiple champers, the surface 23 of the layer 16 can be kept relatively flat providing a homogenous lift of the face mask 8 across the face when filling the pockets with water. In FIG. 14b the layer 16 comprising the water pocket system is shown with one single water pocket 25. Due to the single water pocket the surface 23 of the layer comprising the water pocket will be slightly convex when filled. The number of water pockets 25 can be arbitrarily chosen form 1 to many, and the shape of the pockets 25 may also be any appropriate shape, e.g. similar to ice-cube bags.

Figure 15:
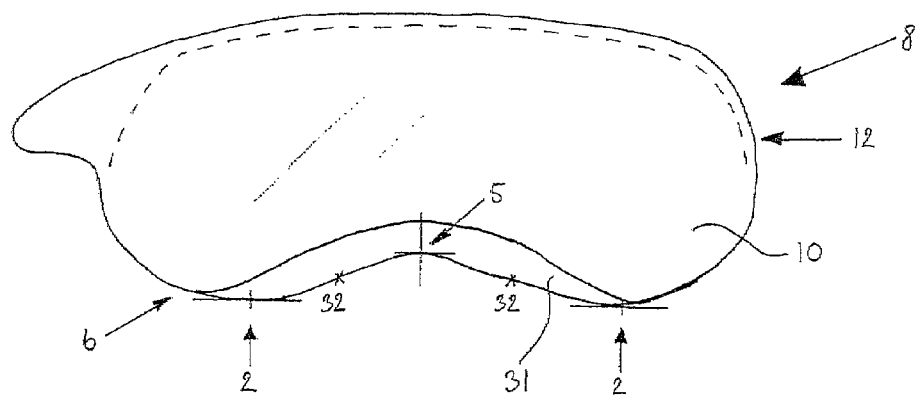
FIG. 15 is a top plan view of an embodiment of the present invention with a gutter system
Figure 16A:
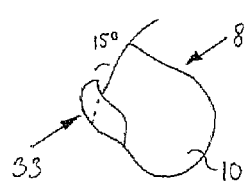
FIG. 16a is a pictorial cross section of a face mask according to the present invention with an almost close loop gutter system.
Figure 16B:
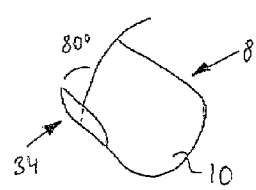
FIG. 16b is a pictorial cross section of a face mask according to the present invention with an almost open gutter system.
Figure 16C:
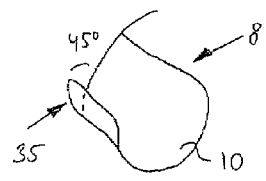
FIG. 16c is a pictorial cross section of a face mask according to the present invention with a 45 degree open gutter system.
Figure 16C:
Figure 16C:
Figure 16C:

FIGS. 15 and 16 show an embodiment of a face mask 8 according to the present invention provided with a gutter system 31.

The face mask 8 has a gutter 31 placed at the convex-concave-convex (wave-shaped) bottom edge 6 of the second surface facing away from the user's face direct water away from the nose and mouth region and towards the convex points 2 on the face mask 8 essentially preventing dripping of water in front of the mouth (children like to talk hence it is important to avoid getting a lot of water in the mouth).

The gutter 31 does preferable stretch from the convex point 2 at the left side of the face mask 8 over the concave point 5, to the convex point 2 at the right side of the face mask 8, but a shorter gutter 31 e.g. from a point 32 on the left side of the face mask 8 to a corresponding point 32 on the right side of the face mask 8 will give a similar effect. The height of the gutter 31 may be the same over the full length or vary and be lower at the end points. The bending of the gutter may vary from nearly a full sized circle 33 to a 90 degrees open circle 34. Preferable the bending of the gutter is app. 45 degrees for obtaining optimal diversion of the water flow.

Figure 17:
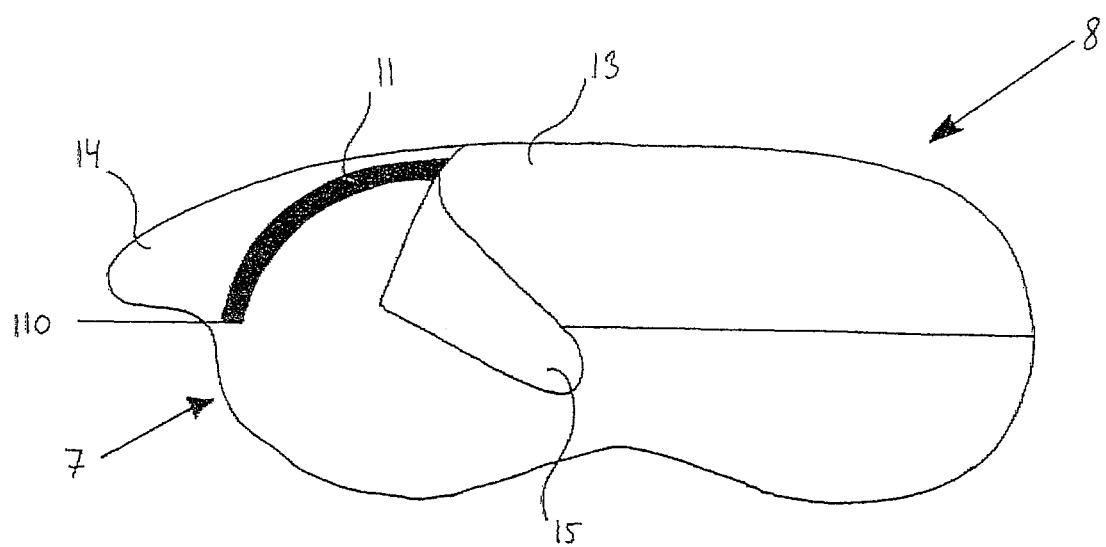
FIG. 17 is a pictorial view of removal of release-liner with removal grip.

FIG. 17 shows a face mask 8 according to the present invention provided with an application and removal grip 14. The application and removal grip 14 is preferable the size of a thumb for optimal hold, easy application of the face mask 8 and easy removal of the face mask 8 after use. The grip 14 should preferable be placed along the left side 7, with the bottom of the grip starting at end point 110 of the adhesive strip to secure a regular even draw (single direction) minimizing the peel force when removing the release liner 13 from the adhesive 11—and minimizing the peel force when removing the face mask 8 from the face of the wearer, securing optimal gentleness.

As shown in FIG. 17, the adhesive strip 11 may be protected by a removable release liner 13 for protecting the adhesive before use. The face mask 8 is designed to make hair wash unproblematic; hence application of the face mask 8 before use, and removal of the face mask 8 after use is made very simple. The release liner 13 is removed by pulling the release liner grip 15 away from the removal grip 14 on the face mask 8. The regular even draw, that is initiated at point 110 (single direction) minimises the peel force and thereby makes it easy to remove the release-liner 13 from the face mask 8. When the release-liner 13 is removed the face mask 8 can be placed in the forehead, and is ready to be used.

After use, the face mask 8 is removed by pulling the removal grip 14 and due to a regular even pull (single direction) along the adhesive strip the mask may easily be removed implying minimum pulling of the skin.

FIGS. 18-21 show schematically the results of experiments examining the flow of water on the surface of different embodiments of face masks.

EXAMPLE

Comparison of Flow of Water from Face Protection Masks Having Differently Shaped Bottom Edges Shields made from PU sheet and specimen having a bottom edge having one central convex part, having a bottom edge having a convex-concave-convex shape, having a linear horizontal bottom edge and having one convex bottom part offset the centre were tested.

For each specimen water was sprayed onto the shield using a shower, and the pattern of draining off of water was noted. The results are presented in FIGS. 18-21.

Figure 18:
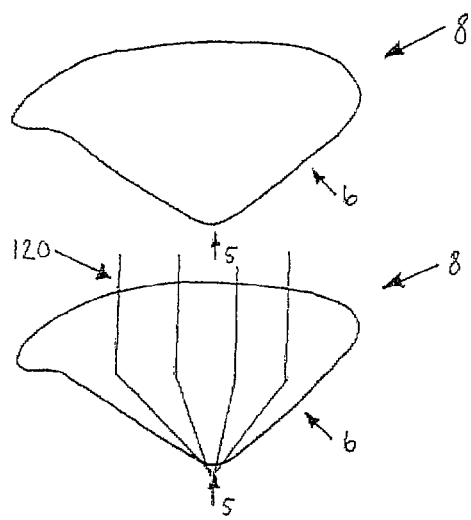
FIGS. 18-21 schematically show the flow of water on different embodiments of face masks.

The result from testing the specimen having bottom edge having one central convex part appears from FIG. 18 showing that when the water streams 120 hit the face mask 8, water streams towards the tip 5 of the convex bottom edge 6, creating a draining of water from the tip 5 over the nose and mouth region.

Figure 19:
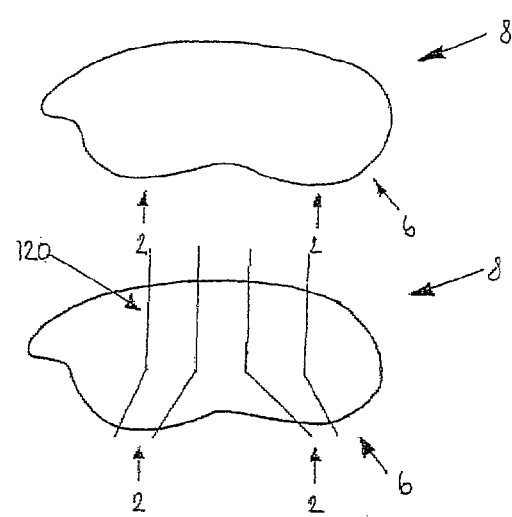

The result from testing the specimen having a bottom edge having convex-concave-convex shape appears from FIG. 19 showing that when the water streams 120 hit the face mask 8, water streams towards the convex points 2 on the bottom edge 6, leading the water away from the nose and mouth region minimising the amount of water that drips in front of the nose and mouth region and thus may enter the mouth.

Figure 20:
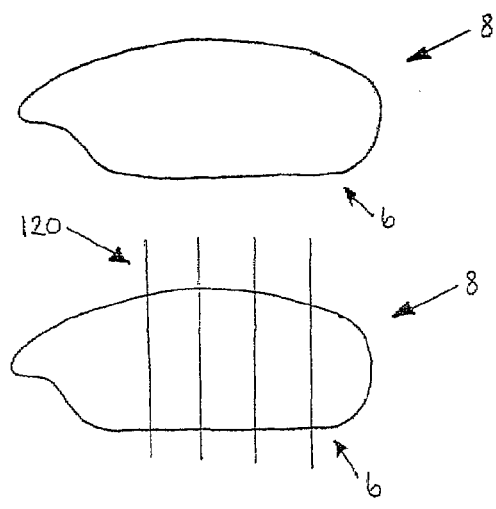

The result from testing the specimen having a linear horizontal bottom edge appears from FIG. 20 showing that when the water streams 120 hit the face mask 8, water streams towards the bottom edge 6 in essentially linear lines. The amount of water dripping in front of the nose and mouth is smaller than when using the face mask of FIG. 18, but larger than when using the face mask of FIG. 19.

Figure 21:
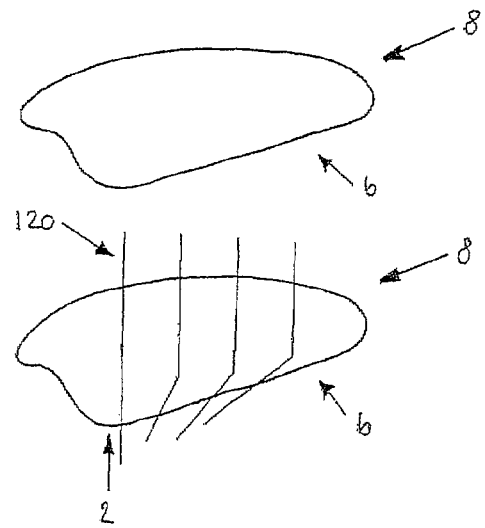

The result from testing the specimen having a bottom edge having one convex bottom part offset the centre appears from FIG. 21 showing that when the water streams 120 hit the face mask 8, water streams towards the convex point 2 on the bottom edge 6. The water that hits the mask on the short side opposite the convex point mainly streams along the edge 6 towards the convex point 2, hence considerable more water drips in front of the nose and mouth in this case than when using the face mask of FIG. 19.

SUMMARY LISTING OF REFERENCES

WO 2004/010912 (SHARKLIDS EYEGEAR LLC)
U.S. Pat. No. 4,367,732 (Coloplast A/S)
U.S. Pat. No. 3,339,546 (E. R. Squibb and Sons, Inc.)
WO 2005/033198 (Coloplast A/S)
U.S. Pat. No. 4,856,535 (Forbes)
WO 2005/110147 (Christian Erdinger).

The invention claimed is:

1. A protective face mask comprising:
an eye-protecting shield made essentially from a plastics material, the eye-protecting shield being dimensioned to cover at least the eye portions of a human wearer, the eye-protecting shield having a perimeter having an upper part and a lower part defining a first surface facing the wearer's face, and a second surface facing away from the wearer's face, said mask having a centre line;
an adhesive forming an adhesive strip attached to the first surface of the eye-protecting shield for providing a substantially watertight and releasable sealing engagement between at least a portion of the perimeter forming an upper edge of the face mask and at least a portion of the skin of the wearer's face, wherein
the upper part of the perimeter of the mask is provided with a continuous layer of adhesive along the perimeter, and the lower part of the perimeter of the mask is free of adhesive,
the lower part of the perimeter forms a bottom edge of the mask and is provided with a convex-concave-convex bottom edge having two convex parts forming projections offset from the centre line of the mask and having a concave part,
the mask extends along with the contour of the wearer's face from the forehead to cheekbones and the lower perimeter thereof extends to minimum the tip of the wearer's nose and no longer than a level of the wearer's mouth, and
the convex-concave-convex bottom edge has two lowest points respectively at the two convex parts and a highest point in the concave part and between the two lowest points, and a distance between the highest point and each of the two lowest points is from 0.5 to 2 cm.

2. The face mask according to claim 1, wherein the upper part of the perimeter of the mask has a generally convex shape.

3. The face mask according to claim 1, wherein the eye-protecting shield is made from one single piece of material, with said adhesive being attached to said first surface of the single-piece eye-protecting shield.

4. The face mask according to claim 1, wherein the adhesive is capable of adhering to wet and/or substantially dry skin.

5. The face mask according to claim 1 comprising an adhesive from a group consisting of hydrocolloid, hydrogel and any combination thereof.

6. The face mask according to claim 1, wherein the adhesive provides a resealable sealing engagement with the skin of the wearer's face.

7. The face mask according to claim 1, wherein the adhesive comprises a flexible adhesive structure.

8. The face mask according to claim 1, wherein an expandable layer is provided between the adhesive strip and the shield, said expandable layer being provided with one or more pockets having at least one opening adjacent to the upper edge of the mask.

9. The face mask according to claim 8, wherein the expandable layer comprises a series of individual pockets.

10. The face mask according to claim 8, wherein the expandable layer comprises a series of interconnected pockets.

11. The face mask according to claim 1, wherein the central part of the bottom edge of the mask is provided with a gutter system.

12. The face mask according to claim 1, wherein the eye-protecting shield is flexible, light and transparent.

13. The face mask according to claim 1, wherein the eye-protecting shield is flexible and capable of conforming to the shape and contour of the wearer's face in the region of the wearer's eyes and nose.

14. The face mask according to claim 1, wherein the plastics material of the eye-protecting shield is provided with a coating with one or more coatings selected from the group consisting of
coatings protecting against ultra-violet penetration;
coatings providing water-shedding or hydrophobic properties; and
coatings providing anti-dew properties.

15. The face mask according to claim 1, wherein a projection removal grip is located on a same level as an end of the adhesive strip.

16. The face mask according to claim 1, wherein a release-liner is provided with a projection removal grip located on a same level as a removal grip of the face mask.

17. The face mask according to claim 1, wherein the layer of adhesive forms an adhesive strip along the perimeter until a level of a corner of the wearer's eye.

* * * * *

UNITED STATES PATENT AND TRADEMARK OFFICE
CERTIFICATE OF CORRECTION

| | |
|---|---|
| PATENT NO. | : 8,458,812 B2 |
| APPLICATION NO. | : 12/857052 |
| DATED | : June 11, 2013 |
| INVENTOR(S) | : Helle Kayerod |

It is certified that error appears in the above-identified patent and that said Letters Patent is hereby corrected as shown below:

ON THE TITLE PAGE:

Please insert the following:

-- (30)     Foreign Application Priority Data

Aug. 29, 2006     (EP) .................. 06017965.2 --.

Signed and Sealed this
Fifteenth Day of October, 2013

Teresa Stanek Rea
*Deputy Director of the United States Patent and Trademark Office*